United States Patent
Antoncic et al.

(10) Patent No.: US 8,697,741 B2
(45) Date of Patent: Apr. 15, 2014

(54) PROCESS FOR THE PREPARATION OF AMORPHOUS CALCIUM SALT OF ATORVASTATIN

(75) Inventors: Ljubomir Antoncic, Ljubljana (SI); Gorazd Sorsak, Ljubljana (SI); Anton Copar, Smartno pri Litijl (SI)

(73) Assignee: LEK Pharmaceutical D.D., Ljubljana (SI)

( * ) Notice: Subject to any disclaimer, the term of this patent is extended or adjusted under 35 U.S.C. 154(b) by 312 days.

(21) Appl. No.: 12/397,981

(22) Filed: Mar. 4, 2009

(65) Prior Publication Data

US 2009/0182030 A1    Jul. 16, 2009

Related U.S. Application Data

(63) Continuation of application No. 10/552,562, filed as application No. PCT/SI2004/000019 on Apr. 9, 2004.

(30) Foreign Application Priority Data

Apr. 11, 2003  (SI) .................................... 200300100
Jun. 6, 2003   (SI) .................................... 200300138

(51) Int. Cl.
  *C07D 207/34*  (2006.01)
  *A61K 31/40*  (2006.01)

(52) U.S. Cl.
  USPC .......................................... 514/423; 548/537

(58) Field of Classification Search
  None
  See application file for complete search history.

(56) References Cited

U.S. PATENT DOCUMENTS

2003/0149279 A1    8/2003   Kumar et al.

FOREIGN PATENT DOCUMENTS

| WO | WO-9703960 | 2/1997 |
| WO | WO-0071116 | 11/2000 |
| WO | WO-0142209 | 6/2001 |
| WO | WO03/018547 | * 8/2001 |
| WO | WO-0259087 | 5/2002 |
| WO | WO-02057228 | 7/2002 |
| WO | WO-03018547 | 3/2003 |
| WO | WO-03068739 | 8/2003 |
| WO | WO-03093233 | 11/2003 |
| WO | WO 2006/037125 | * 9/2005 |

OTHER PUBLICATIONS

Chawla et al., "Challenges in Polymorphism of Pharmaceuticals", CRIPS vol. 5, No. 1, Jan.-Mar. 2004 (4 pgs.).
Newman et al., "Solid-state analysis of the active pharmaceutical ingredient in drug products", DDT vol. 8, No. 19, Oct. 2003, p. 898-905.

* cited by examiner

*Primary Examiner* — Sun Jae Yoo
(74) *Attorney, Agent, or Firm* — Merchant & Gould P.C.

(57) ABSTRACT

A process for the preparation of amorphous atorvastatin calcium. The process includes providing a reaction mixture having a pH between 6.5 and 8.0 containing a sodium salt of atorvastatin and tetrahydrofuran. A non-cyclic chlorinated organic solvent selected from the group consisting of dichloromethane, trichloroethane, tetrachloroethane and chloroform or addition of cyclic hydrocarbon solvent selected from the group consisting of cyclohexane, cyclopentane and methyl cyclohexane is added to provide a mixture of organic solvents. An equivalent or an excess quantity of a source of calcium ions selected from the group consisting of calcium acetate and calcium chloride is added. Amorphous atorvastatin calcium is isolated from an organic phase comprising the mixture of organic solvents.

8 Claims, 5 Drawing Sheets

PROCESS FOR THE PREPARATION OF AMORPHOUS CALCIUM SALT OF ATORVASTATIN

CROSS REFERENCE TO PRIOR APPLICATIONS

This application is a continuation of application Ser. No. 10/552,562, filed on Oct. 11, 2005, which is a U.S National Phase application under 35 U.S.C. §371 of International Application No. PCT/SI2004/000019, filed on Apr. 9, 2004 and which claims benefit to Slovenian Patent Application No. P-200300100, filed on Apr. 11, 2003 and to Slovenian Patent Application No. P-200300138, filed on Jun. 6, 2003. The International Application was published in English on Oct. 21, 2004 as WO 2004/089895 A1 under PCT Article 21(2).

FIELD OF THE INVENTION

Present invention relates to the field of organic synthesis, more exactly, it relates to the manufacturing process for preparing pharmaceutically acceptable salt of atorvastatin in amorphous form. In a technologically simple way, the invention enables the preparation of amorphous atorvastatin calcium without intermediate isolation of solid crystalline atorvastatin calcium.

PRIOR ART

Atorvastatin calcium, a substance with chemical name of hemicalcium salt (R—(R*,R*))-2-(4-fluorophenyl)-β-δ-dihydroxy-5 (1-methylethyl)-3-phenyl-4((phenylamino)carbonyl)-1H-pyrol-1-heptanoic acid and with the chemical formula

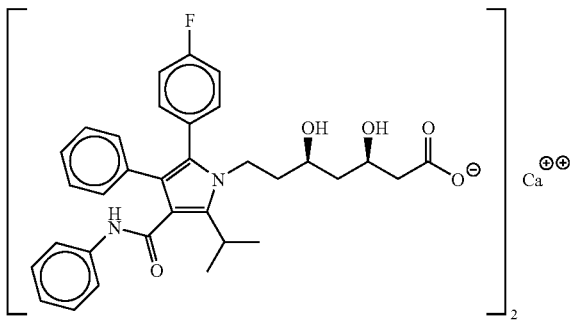

is known as inhibitor of 3-hydroxy-3-methylglutaryl-coenzyme A reductase (HMG-CoA reductase), that is an enzyme catalyzing the intracellular synthesis of cholesterol. Thus the HMF-CoA reductase inhibitors are especially applicable at treating hypercholesterolemia and hyperlipidemia.

The substance atorvastatin was first described in U.S. Pat. No. 4,681,893 with a generic formula, its salt atorvastatin calcium, however, having been first disclosed in U.S. Pat. No. 5,273,995. Processes for preparing atorvastatin, salts thereof and key intermediates have been described in several patent applications, such as international publications WO 89/07598, WO 92/06968, WO 93/07115, WO 94/20492. As active pharmaceutical substance atorvastatin, usually in the form of a calcium salt, is present in the pharmaceutical form, such as tablets, capsules, powders, and other forms of oral application of medicament.

Atorvastatin calcium may exist in different crystal forms described in different patent applications, such as international publications WO 97/03958, WO 97/03959, WO 01/36384, WO 02/41834, WO 02/43732, WO 02/51804, WO 02/57229, WO 03/004470. The great number of known crystal forms of atorvastatin calcium indicates the fact that the substance is more or less stable in several polymorphous forms.

It is known that atorvastatin calcium obtained by different manufacturing processes is precipitated as low crystalline solid substance having a poorly defined structure. A consequence thereof are relatively badly repeatable processes for preparing the final substances with regard to the polymorphous form, i.e., pharmaceutical active substances prepared in this way are not suitable to be incorporated into pharmaceutical forms, which require strict repeatability in regard to the polymorphous form of active substance.

Processes of preparing amorphous atorvastatin calcium have been disclosed in different patent applications, such as WO 97/03960, WO 00/71116, WO 01/28999, WO 01/42209, WO 02/057228, WO 03/018547. These processes proceed over previously isolated crystal atorvastatin calcium, or an undefined mixture of crystal and amorphous atorvastatin calcium. Isolation of substance in crystalline or non-crystalline form and further amorphization represent a two-step synthesis process, which lowers the yield process as a whole.

Processes of preparing non-crystal atorvastatin calcium without intermediate isolation of solid product have been disclosed in international applications WO 01/12706, WO 02/059087, WO 02/083638 and WO 02/083637. Said amorphous forms are not entirely amorphous, these being structures with crystallization nuclei, which in different references are characterized as amorphous. In international patent application WO 03/018547 there is disclosed a process for preparing amorphous atorvastatin calcium with aqueous alkaline or earth alkaline metal bases with advantageous use of calcium hydroxide.

It is known that the amorphous form of an individual pharmaceutical active substance has different dissolution characteristics and a different bioavailability in comparison to crystalline forms (Konno T., Chem. Pharm. Bull., 1990, 38:2003-2007). For some therapeutical indications, bioavailability is one of the key parameters at determining the forms of the pharmaceutical active substance entering the pharmaceutical form. It is generally known that pharmaceutical active substances in amorphous form are better soluble, or dissolve more quickly than crystalline ones. An advantage of amorphous pharmaceutical active substance over crystalline one is especially distinct at poorly soluble substances, such as e.g., atorvastatin calcium, which is expressed in a higher biological applicability of the active substance.

SHORT DESCRIPTION OF THE DRAWINGS

DESCRIPTION OF THE INVENTION WITH EXAMPLES

Figure 1:
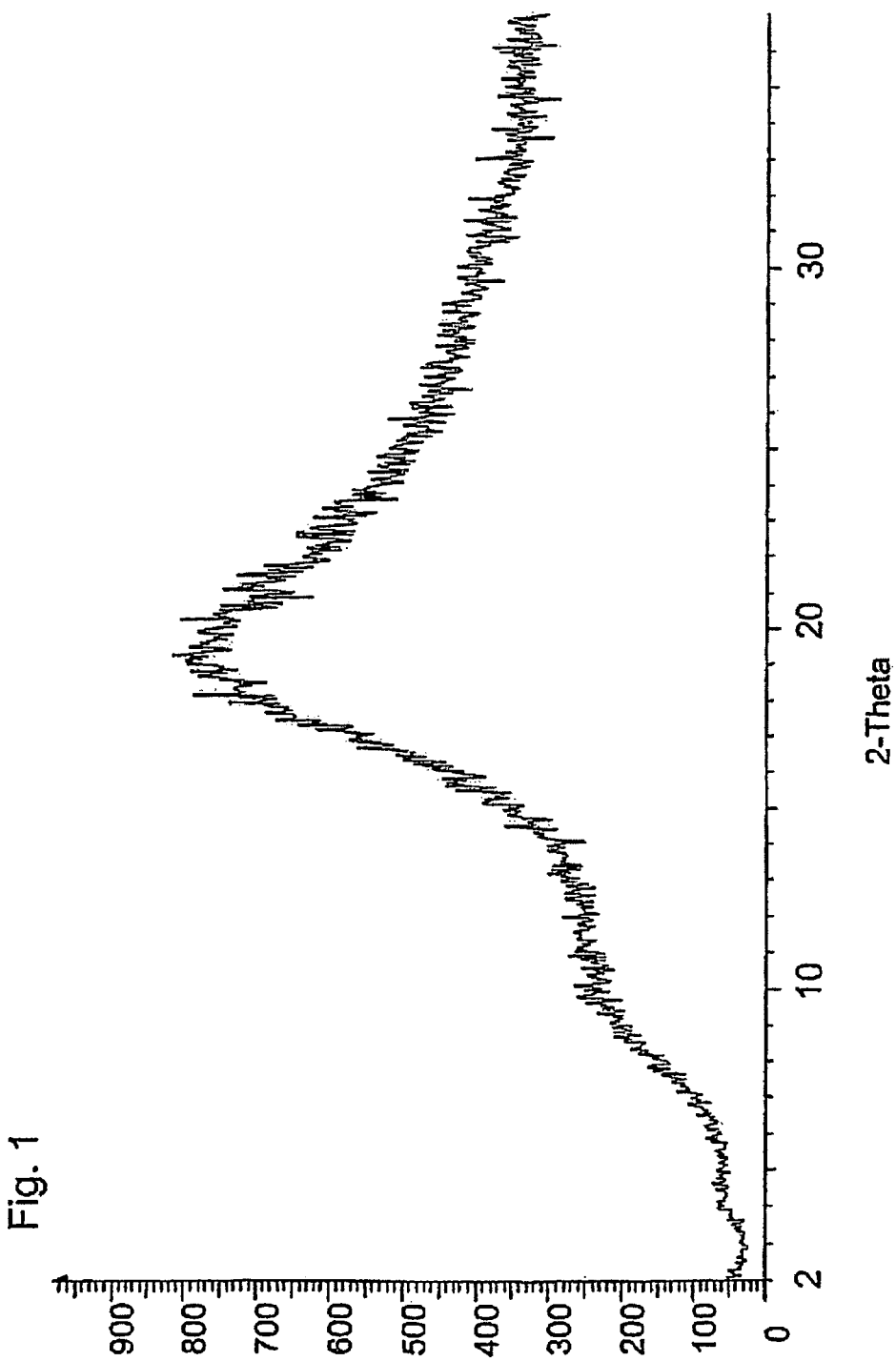
FIG. 1 shows an X-ray powder diffractogram of atorvastatin calcium salt obtained by the process according to Example 1.

In view of above-mentioned advantages of amorphous atorvastatin, such as better bioavailability and better solubility, there is present a constant need to prepare amorphous atorvastatin calcium in one step without isolation of the intermediate solid product, which essentially contributes to lowering the production cost. We have ascertained that the key factor in this process is the selection of the organic solvent used in the step of forming calcium salt of atorvastatin, i.e., prior to precipitation thereof. We found out that atorvastatin calcium is very well soluble in mixture of chlorinated organic solvents selected from the group consisting of chloroform, dichloromethane, trichloroethane, or tetrachloroethane and a non-hydroxylic organic solvent, such as e.g., tetrahydrofuran and water. Additionally surprisingly we have found that atorvastatin calcium in spite of its ionic nature is well soluble in a mixture of cyclic hydrocarbon solvent selected from the group consisting of cyclohexane, cyclopentane or methyl cyclohexane and non-hydroxylic organic solvent, such as, e.g., tetrahydrofuran, and water.

Especially advantageous is the fact that in said mixture of solvents the substance is better soluble than in a water solution. Consequently, in the step of preparing calcium salt of atorvastatin with the aid of an inorganic source of calcium ions, a systems of solvents may be used—a chlorinated organic solvent/an organic non-hydroxylic solvent/water or a cyclic hydrocarbon solvent/an organic non-hydroxylic solvent/water, without precipitation having taken place of less soluble compounds, such as calcium inorganic salts and sodium salt of atorvastatin, which ensures from alkalization of the reaction mixture with sodium hydroxide.

The main object of the present invention is, consequently, to prepare an amorphous form of atorvastatin calcium without intermediate isolation or precipitation, respectively, of crystalline or undefined mixture of crystalline and amorphous atorvastatin calcium.

This object is attained in that the formation of atorvastatin calcium salt is carried out in a solvent mixtures, namely, solvent mixture of chlorinated organic solvent and an organic non-hydroxylic solvent and water or solvent mixture of cyclic hydrocarbon solvent and an organic non-hydroxylic solvent and water.

In the step of formation of calcium salt of atorvastatin, no precipitation of calcium or any other salt of atorvastatin takes place. Chlorinated organic solvents or cyclic hydrocarbon solvents may be used in quantities which in a mixture with an organic non-hydroxylic solvent and water ensure total solubility of all components until the last synthesis step when atorvastatin calcium salt precipitates from the solution with an addition of solvent in which the product is low soluble, or is insoluble, respectively.

Different calcium sources may be used for the preparation of calcium salt of atorvastatin, as for example water solution of calcium acetate or calcium chloride, respectively. The present invention can use calcium acetate or calcium chloride. Namely, by using some of other calcium sources, such as, e.g., calcium hydroxide, it is necessary before the precipitation of atorvastatin from the organic solvents mixture to filtrate the mixture due to the circumstance that calcium hydroxide is less soluble in chlorinated organic solvents in comparison to calcium acetate. An additional disadvantage of presence of calcium hydroxide in the reaction mixture with the chlorinated organic solvent or cyclic hydrocarbon solvents is in the appearance of reaction mixture turbidity, which effects on the forming of the desired amorphous atorvastatin and the amount of impurities present in the final product, as well. In this case the product should, for use in a pharmaceutical formulation, be additionally purified.

A further object of the present invention is the preparation of amorphous form of atorvastatin calcium according to the process, which includes the following steps:

a) Preparation of a neutral reaction mixture containing sodium salt of atorvastatin which is dissolved in a mixture of non-hydroxylic organic solvent, such as, e.g., tetrahydrofuran, and water in an 8:1 ratio. The obtained reaction mixture shows a pH in the range between 6.5 and 8.0.

b) To the obtained solution there is added a onefold to a fivefold volume with respect to the existing volume of chlorinated organic solvent selected from the group consisting of dichlormethane, tetrachloroethane, trichloroethane, chloroform, preferably chloroform or cyclic hydrocarbon solvent selected from the group consisting of cyclohexane, cyclopentane or methyl cyclohexane, preferably cyclohexane, and 0.5 fold to a twofold volume of saturated water solution of sodium chloride with respect to the existing volume. Optionally in case chlorinated organic solvents are used and necessary in case cyclic hydrocarbon solvents are used, both organic and water layer are separated in a funnel separator. After the separation the organic layer is saved for further use in the preparation process.

c) To the reaction mixture of previously prepared sodium salt of atorvastatin an equivalent or an excess quantity of calcium ions source is added. As source of calcium ions, water solution of calcium acetate or calcium chloride, preferably calcium acetate is used. The product atorvastatin calcium salt is formed in the solution.

d) Isolation of atorvastatin calcium salt proceeds according to hitherto known and disclosed processes.

An object of the present invention is also the preparation of amorphous form of atorvastatin calcium from the compound of formula I or II without intermediate isolation or crystal or undefined mixture of crystal and amorphous atorvastatin calcium. An advantage of this process is that the it assures a pharmaceutical quality of the final product without special additional purification of the obtained substance.

According to the process, which is object of present invention, the compound with the formula I or II

I

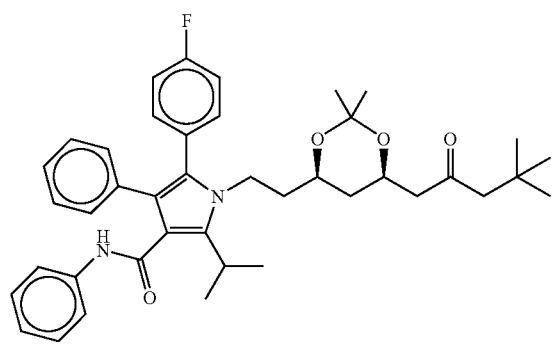

-continued

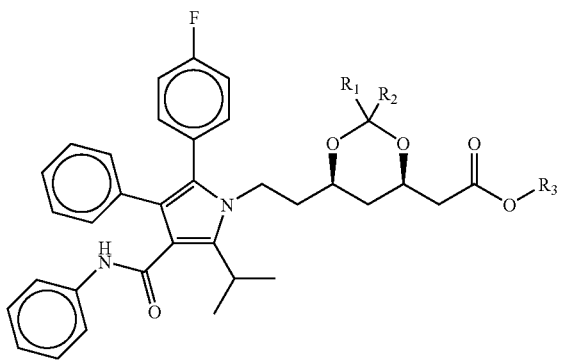

wherein R₁ and R₂ may independently represent hydrogen, alkyl with one to three carbon atoms, phenyl, or R₁ or R₂ are taken together as (—CH₂)$_n$—, wherein n may be 4 or 5; R₃ may represent straight or branched chain alkyl of from one to eight carbon atoms or cycloalkyl of from three to six carbon atoms, R₃ may represent tert-butyl, tert-amyl or α,α-dimethylbenzyl.

Group O—R₃ may be substituted by the group with the formula:

wherein R₄ and R₅ may independently represent
-alkyl with one to ten carbon atoms,
-cyclopropyl,
-cyclobutyl,
-cyclopentyl,
-cyclohexyl,
-benzyl or phenyl,
or R₄ in R₅ are taken together to form:
—(CH₂)₄—,
—(CH₂)₅—,
—(CH(R⁶)—CH₂)₃—,
—(CH(R⁶)—CH₂)₄—,
—(CH(R⁶)—(CH₂)₂—CH(R⁶))—,
—(CH(R⁶)—(CH₂)₃—CH(R⁶))—,
—CH₂—CH₂—O—CH₂—CH₂—,
—CH(R⁶)—CH₂—O—CH₂—CH₂—,
—CH(R⁶)—CH₂—O—CH₂—CH₂(R⁶)—,
wherein R⁶ represents alkyl with one to four carbon atoms, is dissolved in a non-hydroxylic solvent, such as e.g., tetrahydrofuran.

The obtained solution is acidified and stirred at a temperature between 5 and 40° C., preferably at room temperature until it is by thinlayer chromatography no longer possible to detect the starting compounds with the formula I or II. Subsequently, to the solution a base such as, e.g., NaOH is added, until the pH of the solution does not reach a value between 8.0 and 14.0, preferably between 9.0 and 12.0. The obtained solution is mixed at temperature between 5 and 40° C., preferably at room temperature. To the reaction mixture, under intense stirring, an acid is cautiously added until the PH is not in the range between 6.5 and 8.0, preferably 7.8. The formed reaction mixture contains sodium salt of atorvastatin.

To the obtained solution there is added with respect to its existing volume a onefold to a fivefold volume of chlorinated organic solvent selected from the group consisting of dichloromethane, trichloroethane, tetrachloroethane, chloroform, preferably chloroform or cyclic hydrocarbon solvent selected from the group consisting of cyclohexane, cyclopentane, and methyl cyclohexane, and a 0.5 fold to a twofold volume of saturated aqueous solution of sodium chloride with respect to the existing volume. If the cyclic hydrocarbon solvent is used the resulted layers are separated in a funnel separator. The organic layer is saved for further reaction process.

To the reaction mixture or to the organic layer from the separation process an equivalent quantity of calcium ions or excess thereof is added. As source of calcium ions, aqueous solution of calcium acetate or calcium chloride, preferably calcium acetate, is used. To the organic phase of the obtained two-phase system a drying agent, such as, e.g., magnesium sulphate, is added, which is later on removed by filtration. The reaction mixture is further on concentrated to a threshold value when the concentrate is still entirely clear, and during this process, however, the solution must always be entirely clear.

Optionally afterwards the reaction mixture is concentrated to about half of initial volume or a threshold value when the concentrate is still entirely clear, during this process, however, the solution must always be entirely clear. After the twofold of concentrated mixture volume is added a solvent in which atorvastatin is well soluble, i.e., e.g., methanol, ethanol or propanol, and which mixes with used chlorinated organic solvent or cyclic hydrocarbon and a portion of an active coal is also added to the said concentrated mixture. Reaction mixture is mixed for about one hour and filtered. The reaction mixture is further concentrated to a threshold value when the concentrate is still entirely clear, during this process, however, the solution must always be entirely clear.

To the obtained concentrate optionally a twofold up to a sixfold, preferably a threefold, volume of solvent is added to its existing volume, The solvent is such that in which atorvastatin is well soluble, i.e., e.g., methanol, ethanol or propanol, and which is capable of mixing with used chlorinated organic solvent or cyclic hydrocarbon solvent according to the present invention and as well with the solvent used in the next step of precipitating atorvastatin calcium. The reaction mixture is then concentrated to a threshold when the concentrate is still entirely clear, and during this process, however, the solution must always be entirely clear.

Subsequently, a 0.4 fold to a 0.8 fold volume of solvent with regard to the existing volume of solution, preferably a 0.4 fold volume of solvent, in which atorvastatin calcium is not soluble, or is low soluble, is optionally added. As solvent, ether, preferably diisopropyl ether, may be used. The reaction mixture prepared in such a way is under intense stirring poured into a fourfold to eightfold volume of the same solvent with regard to the existing volume, preferably fivefold volume of the same solvent. The reaction mixture is stirred at a temperature from 10 to 30° C., preferably at room temperature. In this step a precipitate of final product—amorphous atorvastatin calcium salt is formed. After removing the solvent by filtration, optionally digerating the product with the organic solvent in which atorvastatin calcium salt is not soluble or is low soluble and washing the product on the filter, final product amorphous atorvastatin calcium salt is dried in vacuum at a temperature from 35 to 45° C.

A further object of the present invention is a pharmaceutical composition and form containing, amorphous atorvastatin calcium obtained according to the present invention, and pharmaceutically acceptable additives. An advantage of atorvastatin calcium obtained according to the present invention lies in that prior to application in pharmaceutical industry, the active substance need not be additionally purified. The pharmaceutical form may cover tablets, capsules, powders, bags, syrups or suspensions for oral, parenteral, rectal, transdermal or nasal application. The pharmaceutical form may be prepared according to the conventional processes known in the prior art.

Amorphous atorvastatin calcium prepared according to the present invention is used for preparing medicaments for the treatment of diseases selected from the group consisting of dislipidemia, hyperlipidemia, hypercholesterolemia, aterosclerosis, ateriosclerosis, cardiovascular disease, coronary arterial disease, coronary heart disease, disorders of blood circulation, inflammation diseases, bone diseases, disorders of processing beta amyloid precursor protein, such as Alzheimer's disease or Down's syndrome.

The present invention is illustrated by the following examples. Although these examples are illustrative, they are not intended to be limiting.

Example 1

4.37 g tert-butyl (6-{2-[2-(4-fluorophenyl)-5-isopropyl-3-phenyl-4-phenylcarbamoylpyrol-1-yl]-ethyl}-2,2-dimethyl-[1,3]dioxin-4-yl)-acetate are dissolved in 35 ml tetrahydrofuran, then 5 ml 10% hydrochloric acid are added, and the solution is stirred at room temperature for 15 hours. 1.2 g solid sodium hydroxide is added, and it is stirred for further 3 hours. pH of the reaction mixture is set to 7.8 with 5N hydrochloric acid at room temperature. To the obtained solution, 50 ml chloroform and 25 ml saturated solution of sodium chloride are added.

To this solution under intense stirring is added a solution of 0.76 g $Ca(OAc)_2.H_2O$ in 10 ml water. The obtained two-phase system is stirred for 30 minutes at 30° C., and the layers are separated. The organic phase is dried with magnesium sulphate and concentrated. To the clear concentrate, methanol is added, and the mixture is once again concentrated.

To the clear concentrate, 5 ml diisopropylether are added. The obtained solution is under intense stirring added into 100 ml diisopropylether. It is stirred for 1 hour and filtrated, after that precipitate is digerated with 50 ml ether, filtrated and the precipitate is on the filter washed with three times 10 ml ether each. The precipitation is dried in vacuum of about 1 mbar at 45° C. overnight.

Obtained are 3.74 g amorphous calcium salt of atorvastatin.

Example 2

4.37 g tert-butyl (6-{2-[2-(4-fluorophenyl)-5-isopropyl-3-phenyl-4-phenylcarbamoylpyrol-1-yl]-ethyl}-2,2-dimethyl-[1,3]dioxin-4-yl)-acetate are dissolved in 35 ml tetrahydrofuran, then 5 ml 10% hydrochloric acid are added, and the solution is stirred at room temperature for 15 hours. 1.2 g solid sodium hydroxide is added, and it is stirred for further 3 hours. pH of the reaction mixture is set 7.8 with 5N hydrochloric acid at room temperature. To the obtained solution, 100 ml dichloromethane and 25 ml saturated solution of sodium chloride are added.

To this solution there is under intense stirring added a solution of 0.76 g $Ca(OAc)_2.H_2n$ 10 ml water. The obtained two-phase system is stirred for 1 hour at 30° C., and the layers are separated. The organic phase is dried with magnesium sulphate and concentrated.

To the clear concentrate, 5 ml diisopropylether are added. The obtained solution is under intense stirring added into 100 ml diisopropylether. It is stirred for 1 hour and filtrated, after that precipitate is digerated with 50 ml ether, filtrated and the precipitate is on the filter washed with three times 10 ml ether each. The precipitate is dried in vacuum of about 1 mbar at 45° C. overnight.

Obtained are 3.09 g amorphous calcium salt of atorvastatin.

Example 3

4.37 g tert-butyl (6-{2-[2-(4-fluorophenyl)-5-isopropyl-3-phenyl-4-phenylcarbamoylpyrol-1-yl]-ethyl}-2,2-dimethyl-[1,3]dioxin-4-yl)-acetate are dissolved in 35 ml tetrahydrofuran, then 5 ml 10% hydrochloric acid are added, and the solution is stirred at room temperature for 15 hours. 1.2 g solid sodium hydroxide is added, and it is stirred for further 3 hours. pH of the reaction mixture is set to 7.8 with 5N of hydrochloric acid at room temperature. To the obtained solution, 50 ml chloroform and 25 ml saturated solution of sodium chloride are added.

To this solution there is under intense stirring added a solution of 0.632 g $Ca(OAc)_2.H_2n$ 10 ml water. The obtained two-phase system is stirred for 30 minutes at 30° C., and the layers are separated. The organic phase is direct magnesium sulphate and concentrated.

To the clear concentrate, 5 ml diisopropylether are added. The obtained solution is under intense stirring added into 100 ml diisopropylether. It is stirred for 1 hour and filtrated, after the precipitate is digerated with 50 ml ether, filtered and the separated precipitate is on the filter washed with three times 10 ml ether each. The precipitate is dried in vacuum of about 1 mbar at 45° C. overnight.

Obtained are 3.65 g amorphous calcium salt of atorvastatin.

Example 4

8.74 g tert-butyl (6-{2-[2-(4-fluorophenyl)-5-isopropyl-3-phenyl-4-phenylcarbamoylpyrol-1-yl]-ethyl}-2,2-dimethyl-[1,3]dioxin-4-yl)-acetate are dissolved in 70 ml tetrahydrofuran, then 10 ml 10% hydrochloric acid are added and the solution is stirred at room temperature for 15 hours. 2.4 g solid sodium hydroxide are added, and it is stirred for further 3 hours. pH of the reaction mixture is set to 7.8 with 5N hydrochloric acid at room temperature. To the obtained solution, 70 ml cyclohexane and 30 ml saturated water solution of sodium chloride are added. The layers are separated.

To the organic phase, under intensive stirring, a solution of 1.52 g $Ca(OAc)_2.H_2$ on 20 ml water is added. The obtained two-phase system is stirred for 1 hour at 30° C., and the layers are separated. The organic phase is dried with $MgSO_4$, $MgSO_4$ is filtered off and the mixture is vaporized to a volume of about 60 ml.

The obtained solution is under intensive stirring added into 200 ml diisopropyl ether. It is stirred for 1 hour and filtrated, precipitate is digerated with 100 ml diethyl ether, filtrated and the precipitate is on the filter washed with three times 20 ml diethyl ether each. The precipitate is dried in a vacuum about 1 mbar at 45° C. overnight.

Obtained are 7.08 g amorphous calcium salt of atorvastatin.

Example 5

8.47 g tert-butyl (6-{2-[2-(4-fluorophenyl)-5-isopropyl-3-phenyl-4-phenylcarbamoylpyrol-1-yl]-ethyl}-2,2-dimethyl-[1,3]dioxin-4-yl)-acetate are dissolved in 70 ml tetrahydrofuran, then 10 ml 10% hydrochloric acid are added, and the solution is stirred at room temperature for 15 hours. 2.4 g solid sodium hydroxide are added, and it is stirred for further 3 hours. pH of the reaction mixture is set to 7.8 with 5N hydrochloric acid at room temperature. To the obtained solution, 70 ml cyclohexane, and 30 ml saturated water solution of sodium chloride are added. The layers are separated.

To the upper layer is under intense stirring added a solution of 1.52 g Ca(OAc)$_2$.H$_2$ in 20 ml water. The obtained two-phase system is stirred for 1 hour at 30° C., and the layers are separated.

The organic phase is dried with MgSO$_4$, MgSO$_4$ is filtrated off and the residue is evaporated to a volume about 50 ml, then 100 ml methanol and 0.874 g of active coal is added. The mixture is stirred for 1 hour, and active coal filtrated off. The mixture is concentrated to a volume of about 20 ml.

To the clear concentrate, 10 ml diisopropylether are added. The obtained solution is under intense stirring added into 200 ml diisopropylether. It is stirred for 1 hour and filtrated, then precipitate is digerated with 100 ml diethyl ether, filtered and the precipitate is on the filter washed with three times 20 ml diethylether each. The precipitate is dried in vacuum of about 1 mbar at 45° C. overnight.

Obtained are 5.83 g amorphous calcium salt of atorvastatin.

Figure 2:
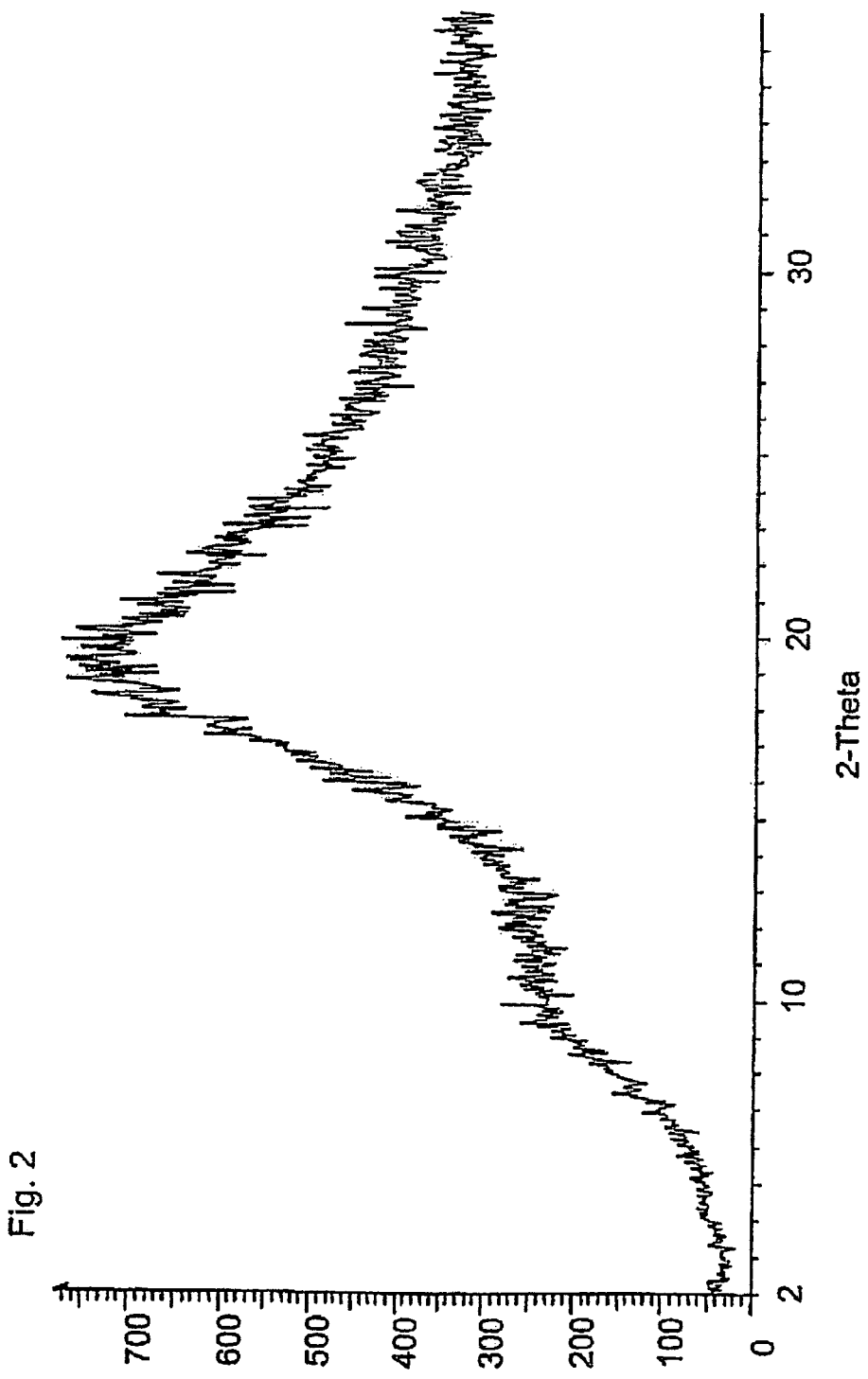
FIG. 2 shows an X-ray powder diffractogram of atorvastatin calcium salt obtained by the process according to Example 2.
Figure 3:
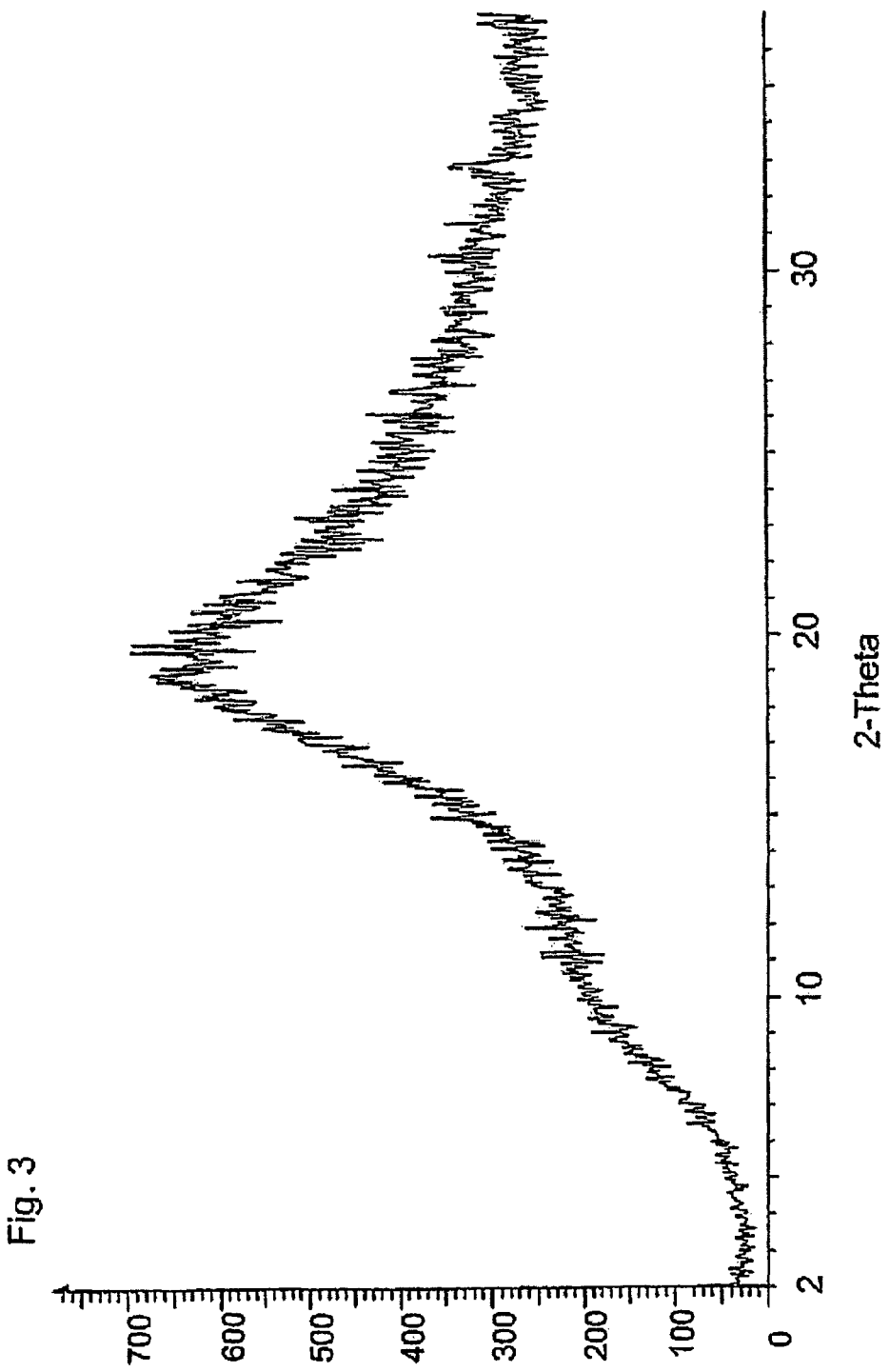
FIG. 3 shows an X-ray powder diffractogram of atorvastatin calcium obtained by the process according to the preparation Example 3.
Figure 4:
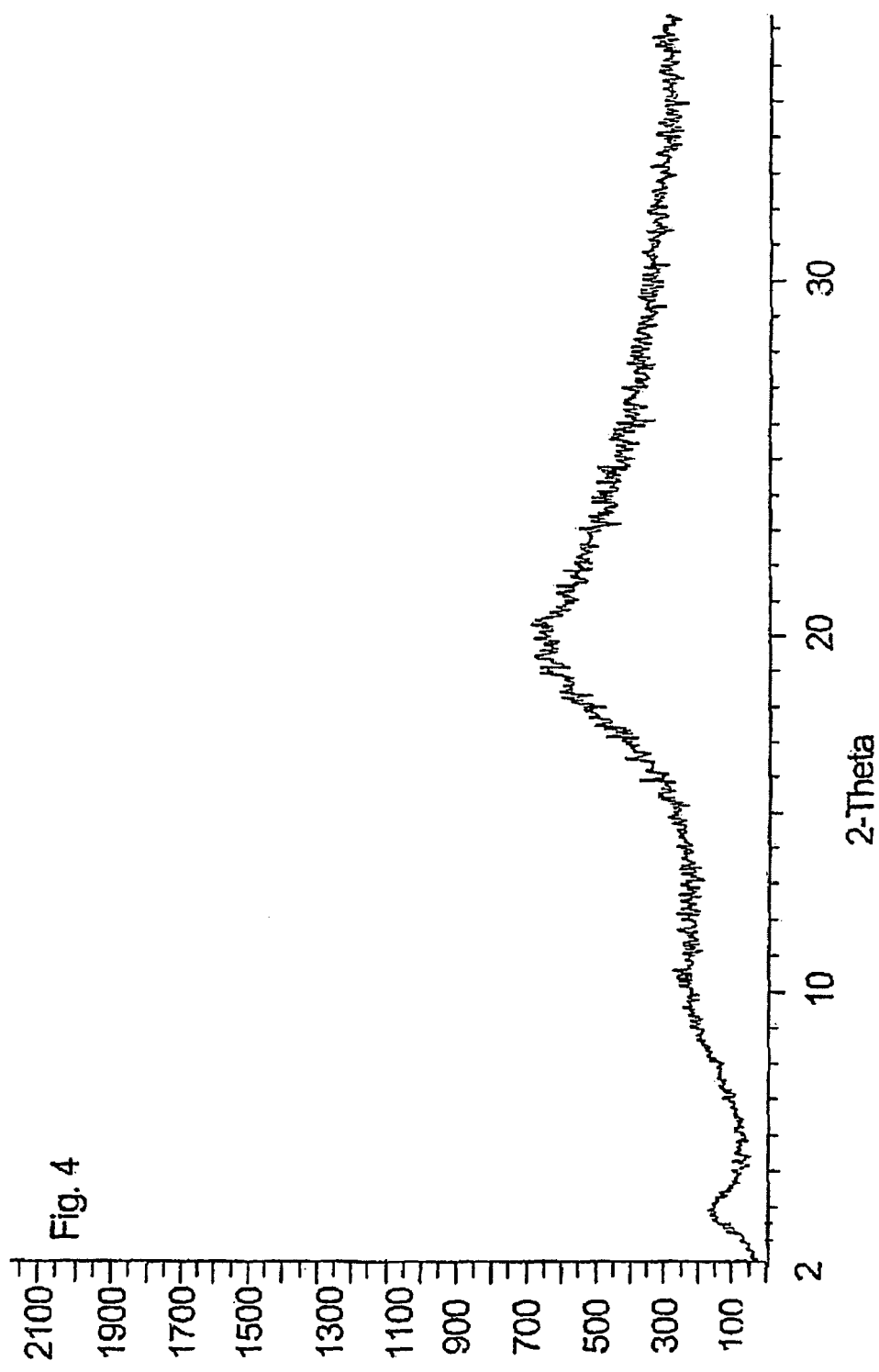
FIG. 4 shows an X-ray powder diffractogram of atorvastatin calcium obtained by the process according to Example 4.
Figure 5:
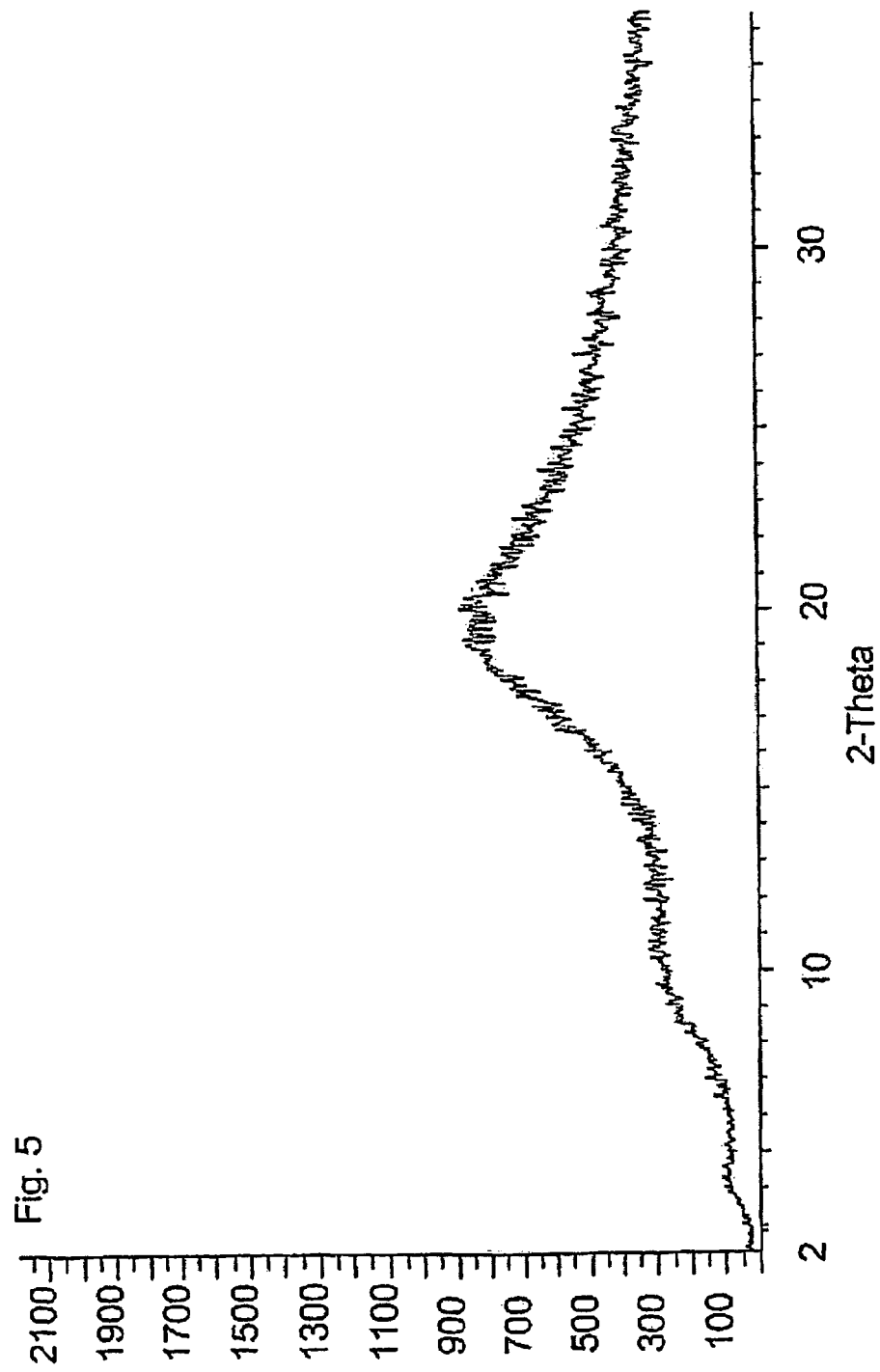
FIG. 5 shows an X-ray powder diffractogram of atorvastatin calcium obtained by the process according to Example 5.

The obtained samples of amorphous atorvastatin calcium salt were analyzed with X-ray powder diffraction analysis, and exhibit X-ray powder diffractograms shown in FIGS. 1 to 5.

The X-ray powder diffraction pattern was collected on Philips PW1710 diffractometer in reflection geometry. The instrument was regularly calibrated with silicon standard. A standard Philips back-loading sample holder was used. Sample storage, mounting, and data collection were performed at room temperature. Instrumental parameters were: CuK$_\alpha$ radiation (30 mA, 40 kV, $\lambda$=1.5406 Å, variable divergence slit (approx. 12×6 mm irradiated area), 0.4 mm receiving slit, graphite monochromator on the secondary side, scintillation counter. Data collection parameters were: 2θ range from 4° to 37°, step scan mode in steps 0.04° 2θ, intergration time 1 second at each step.

What is claimed is:

1. A process for the preparation of amorphous atorvastatin calcium which comprises:
   a) provision of a reaction mixture having a pH between 6.5 and 8.0 containing a sodium salt of atorvastatin and tetrahydrofuran, wherein the reaction mixture is prepared by a process which comprises:
      i) dissolving in tetrahydrofuran a compound of formula I or II:

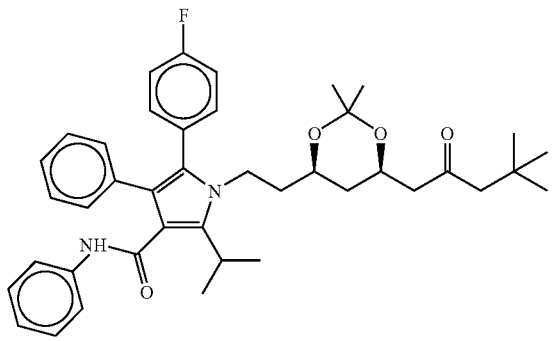

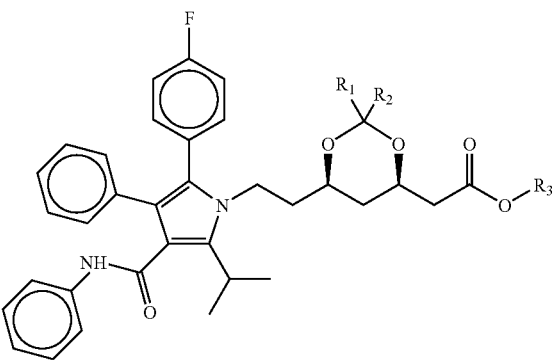

wherein R$_1$ and R$_2$ independently represent hydrogen, alkyl with one to three carbon atoms, phenyl, or R$_1$ in R$_2$ are taken together as —(CH$_2$)$_n$—, wherein n is 4 or 5; R$_3$ represent straight or branched chain alkyl of from one to eight carbon atoms or cycloalkyl of from three to six carbon atoms group and
   ii) converting the compound of Formula I or II to the sodium salt of atorvastatin and providing the reaction mixture having a pH between 6.5 and 8.0;
   b) addition of a non-cyclic chlorinated organic solvent selected from the group consisting of dichloromethane, trichloroethane, tetrachloroethane and chloroform to the reaction mixture to provide a mixture of organic solvents;
   c) addition of an equivalent or an excess quantity of a source of calcium ions selected from the group consisting of calcium acetate and calcium chloride; and
   d) isolation of amorphous atorvastatin calcium from an organic phase comprising the mixture of organic solvents, wherein the isolation step comprises an addition of a ether solvent in which atorvastatin calcium is not soluble or is poorly soluble.

2. A process for the preparation of amorphous atorvastatin calcium according to claim 1, wherein the chlorinated organic solvent is added in a onefold to fivefold quantity based on the existing volume of solution.

3. A process for the preparation of amorphous atorvastatin calcium according to claim 1, further comprising adding simultaneously with the addition of the non-cyclic chlorinated organic solvent a 0.5 fold to a twofold quantity of a saturated aqueous solution of sodium chloride based on the existing volume of solution.

4. A process for the preparation of amorphous atorvastatin calcium according to claim 1, wherein the solvent in which atorvastatin calcium is not soluble or is poorly soluble is diisopropylether.

5. A process for the preparation of amorphous atorvastatin calcium according to claim 1, wherein the isolation of amorphous atorvastatin calcium comprises: a) adding a solvent in which atorvastatin calcium is soluble, b) concentrating the resulting atorvastatin calcium preparation, c) adding an ether solvent in which atorvastatin calcium is not soluble or is poorly soluble, and d) obtaining a precipitant which is in amorphous form.

6. A process for the preparation of amorphous atorvastatin calcium according to claim 5, wherein the solvent in which atorvastatin calcium is soluble is selected from the group consisting of methanol, ethanol and propanol.

7. A process for the preparation of amorphous atorvastatin calcium according to claim 6, wherein the solvent in which atorvastatin calcium is soluble is methanol.

8. A process for the preparation of amorphous atorvastatin calcium according to claim 5, wherein the solvent in which atorvastatin calcium is not soluble or is poorly soluble is diisopropylether.

\* \* \* \* \*